United States Patent
Spireas

(10) Patent No.: US 6,555,551 B1
(45) Date of Patent: Apr. 29, 2003

(54) STABLE FORMULATIONS OF ACE INHIBITORS, AND METHODS FOR PREPARATION THEREOF

(75) Inventor: Spiridon Spireas, Newtown, PA (US)

(73) Assignee: Mutual Pharmaceutical Co., Inc., Newtown, PA (US)

( * ) Notice: Subject to any disclaimer, the term of this patent is extended or adjusted under 35 U.S.C. 154(b) by 31 days.

(21) Appl. No.: 09/598,200

(22) Filed: Jun. 21, 2000

Related U.S. Application Data

(63) Continuation-in-part of application No. 09/492,584, filed on Jan. 27, 2000, which is a continuation-in-part of application No. 09/387,419, filed on Aug. 31, 1999, now abandoned.

(51) Int. Cl.$^7$ .................. A61K 31/44; A61K 31/40; A01N 43/36
(52) U.S. Cl. ......................... 514/299; 514/423
(58) Field of Search ............ 424/401; 514/299, 514/423

(56) References Cited

U.S. PATENT DOCUMENTS

| | | | |
|---|---|---|---|
| 4,716,235 A | 12/1987 | Takahashi et al. ........... 548/533 |
| 4,743,450 A | 5/1988 | Harris et al. ................. 424/440 |
| 4,793,998 A | 12/1988 | Murthy et al. ............... 424/440 |
| 4,830,853 A * | 5/1989 | Murthy et al. ............... 424/440 |
| 4,880,631 A | 11/1989 | Haslam et al. ............... 424/424 |
| 4,886,668 A | 12/1989 | Haslam et al. ............... 424/424 |
| 5,350,582 A | 9/1994 | Merslavic et al. ........... 424/464 |
| 5,350,584 A | 9/1994 | McClelland et al. ........ 424/501 |
| 5,387,696 A | 2/1995 | Kottenhahn et al. ........ 548/533 |
| 5,527,540 A * | 6/1996 | Gergely et al. .............. 424/466 |
| 5,562,921 A | 10/1996 | Sherman ...................... 424/465 |
| 5,573,780 A | 11/1996 | Sherman ...................... 424/464 |
| 5,637,730 A | 6/1997 | Murthy et al. ............... 548/540 |
| 5,686,627 A | 11/1997 | Murthy et al. ............... 548/533 |
| 5,690,962 A | 11/1997 | Sherman ...................... 424/489 |
| 5,789,597 A | 8/1998 | Serra Mortes et al. ...... 546/238 |

FOREIGN PATENT DOCUMENTS

| | | |
|---|---|---|
| CA | 2028665 * | 4/1991 |
| EP | 0 425 892 A2 | 10/1990 |
| WO | PCT/US00/23539 | 12/2000 |

OTHER PUBLICATIONS

Liberman et al. (eds.), *Theory & Practice of Industrial Pharmacy*, 3rd Edition, Philadelphia, PA, 1986.
Remington's Pharmaceutical Sciences, 18th Edition, Easton, PA, Mack Publishing Co., 1990.

* cited by examiner

*Primary Examiner*—Alton Pryor
(74) *Attorney, Agent, or Firm*—Woodcock Washburn LLP

(57) ABSTRACT

The present invention provides stable formulations of ACE inhibitors, especially enalapril maleate, that can be manufactured in a time efficient, cost effective manner. Such formulations can be prepared simply and on a large industrial scale. The present invention also provides methods for the preparation of stable formulations of ACE inhibitors, especially enalapril maleate.

3 Claims, 4 Drawing Sheets

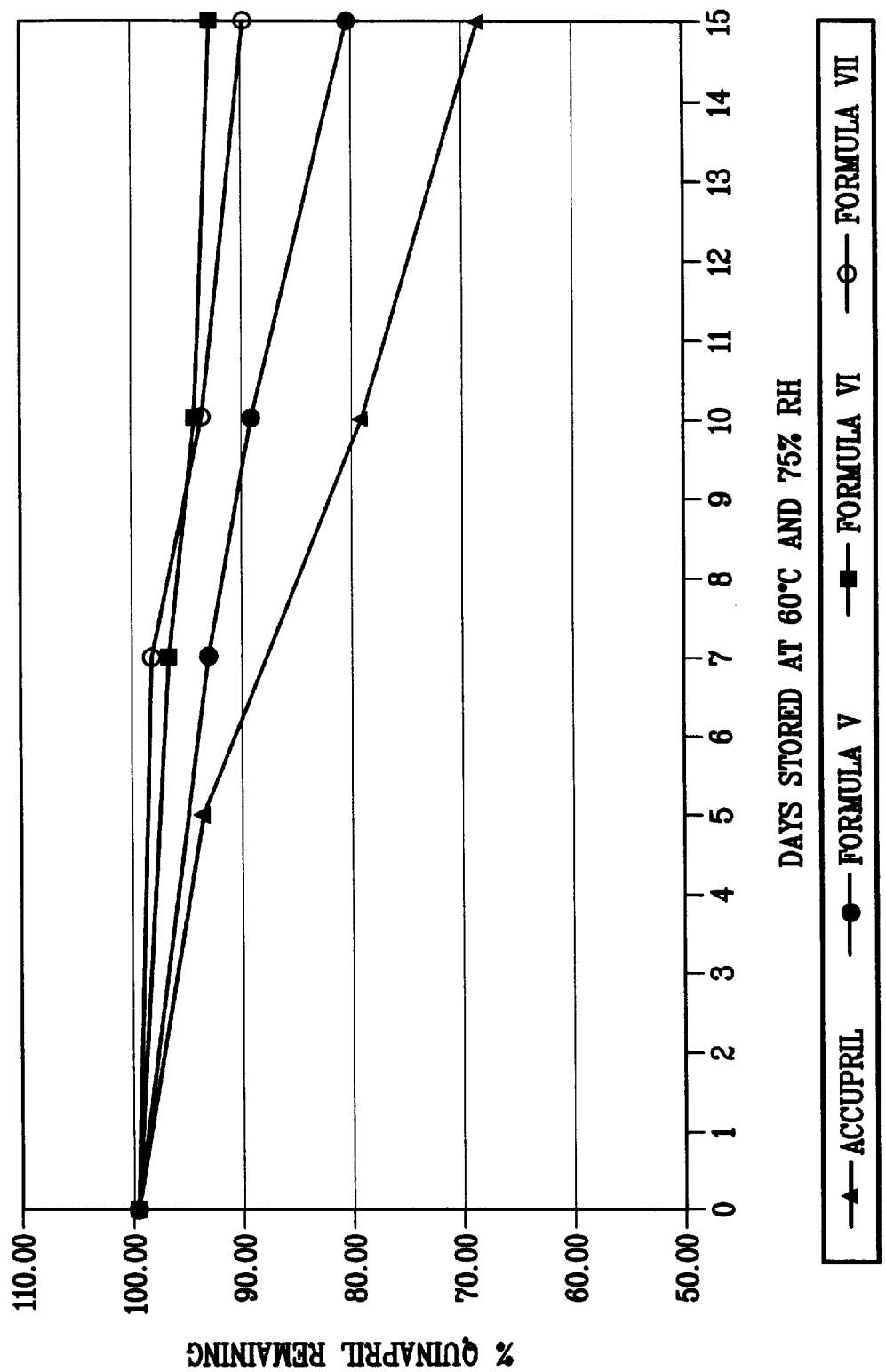

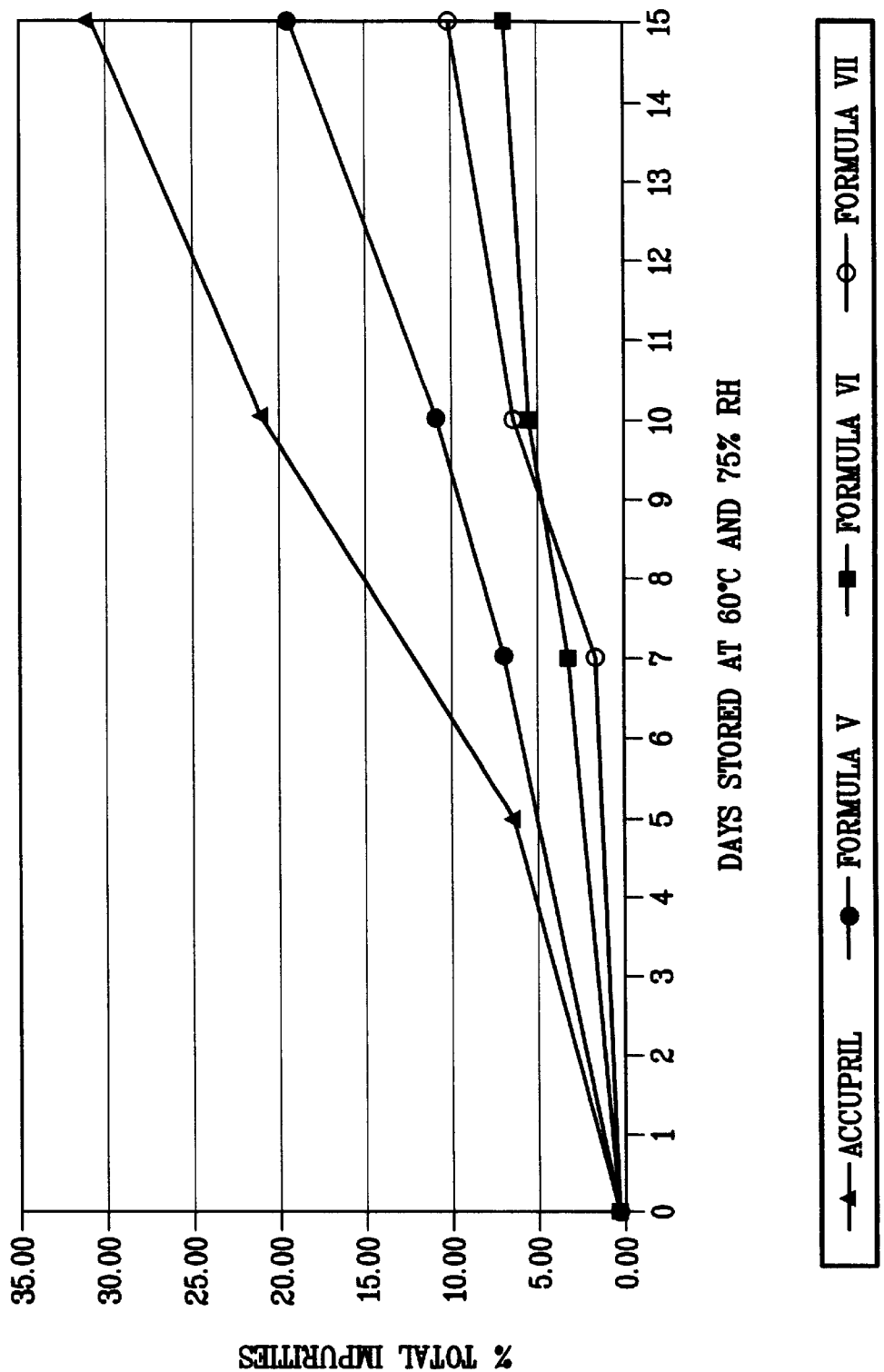

STABLE FORMULATIONS OF ACE INHIBITORS, AND METHODS FOR PREPARATION THEREOF

CROSS REFERENCE TO RELATED APPLICATIONS

This application is a continuation-in-part of U.S. application Ser. No. 09/492,584, filed Jan. 27, 2000, which was a continuation-in-part of U.S. application Ser. No. 09/387,419, filed Aug. 31, 1999 now abandoned.

FIELD OF THE INVENTION

The present invention relates to stable formulations of ACE inhibitors and similar drugs, especially enalapril maleate and quinapril hydrochloride. The present invention also relates to methods for the preparation of stable formulations of ACE inhibitors.

BACKGROUND OF THE INVENTION

ACE inhibitors, or inhibitors of Angiotensin Converting Enzymes, are drugs useful in the treatment of cardiovascular disorders, especially hypertension. However, it has been widely observed that ACE inhibitors are susceptible to breakdown, especially due to degradation and/or cyclization between the time of manufacture and the time of desired usage. Breakdown of ACE inhibitors has been found to occur both in solid and in liquid states. As breakdown of ACE inhibitor increases, the concentration of available, functional ACE inhibitor decreases. Also, at least some of the degradation products of such breakdown are believed to be deleterious. Accordingly, such breakdown is to be avoided.

ACE inhibitors include, but are not limited to, enalapril maleate and similar salts; quinapril hydrochloride and similar salts; benazepril hydrochloride and similar salts; moexipril hydrochloride and similar salts; lisonopril hydrochloride and similar salts; ramipril hydrochloride and similar salts; and indopril hydrochloride and similar salts. Typical breakdown products of ACE inhibitors include, but are not limited to, enalaprilat and/or enalapril-diketopiperazine (DKP) for enalapril species, quinaprilat and/or quinapril-DKP for quinapril drugs, and other breakdown products well-known to those of skill in the art.

Methods for the formulation of enalapril maleate, an ACE inhibitor, into stable solid dosage forms have been previously described. For example, Merslavic et al., in U.S. Pat. No. 5,350,582, describe the formulation of enalapril sodium through the suspension of enalapril maleate in water with certain metal compounds. Full conversion to enalapril sodium is said to be indicated by a final "clear" solution. However, the suspension of enalapril maleate in water is extremely time-consuming due to the low wetability of enalapril maleate. Consequently, the residence time of the drug in the water is high. A high residence time is believed to facilitate significant hydrolysis of the product and lead to a drop in drug purity. Further, following the procedures described by Merslavic et al., high unit dose weights of lactose and starch are required.

Sherman et al., in U.S. Pat. Nos. 5,690,962 and 5,573,780, have described methods for the formulation of enalapril sodium. Instead of dispersing enalapril maleate in water, Sherman et al. describe "dry-blending" the enalapril maleate with an alkaline sodium powder and another powder excipient such as lactose. This "blend" is then granulated with water to initiate the acid-base conversion of enalapril maleate to enalapril sodium. Unlike the process described by Merslavic et al., Sherman provides no easily determinable endpoint of complete conversion of enalapril maleate to enalapril sodium. Therefore, it is likely that significant batch-to-batch variations in purity of the product, i.e., amount of enalapril sodium, will exist in large scale production scenarios. Additionally, the Sherman et al. process may involve a time-consuming conversion of enalapril maleate to enalapril sodium, such that the product is vulnerable to breakdown and a drop in drug purity.

Sherman et al., in U.S. Pat. No. 5,562,921, also describe the manufacture of enalapril maleate formulations with improved resistance to decomposition. These formulations are said to be more resistant to decomposition due to restrictions in the excipients used in the process. However, the excipients set forth by Sherman as offering improved resistance to decomposition may lead to formulations which lack sufficient hardness, an important quality in pharmaceutical formulations.

Harris et al., in U.S. Pat. No. 4,743,450, describe the use of stabilizers to minimize the cyclization, hydrolysis, and coloration of ACE inhibitors.

There remains a long-standing need for stable formulations and methods of preparation of ACE inhibitors. There is a further need for formulations and methods of preparation of ACE inhibitors that minimize breakdown of the product, that are inexpensive and time-efficient, and that have improved uniformity from batch to batch. Additionally, there is a need for methods of preparation and formulations of ACE inhibitors which are greatly reduced in breakdown products during preparation and/or subsequent storage.

SUMMARY OF THE INVENTION

The present invention relates to stable formulations of ACE inhibitors, especially enalapril maleate and similar salts, quinapril hydrochloride and similar salts, and similar drugs. The present invention also relates to time-efficient methods of preparing stable formulations thereof. Further, the present invention provides formulations and methods of preparation of ACE inhibitors that minimize breakdown of the products during preparation and/or subsequent storage thereof. The present invention also relates to products of the methods of preparing stable formulations of ACE inhibitors. The present invention also provides formulations of ACE inhibitors substantially free of harmful and/or undesired breakdown products. It is now possible to prepare such formulations which are substantially free of these contaminants. These and other embodiments of the present invention will readily occur to those of ordinary skill in the art in view of the disclosure herein.

BRIEF DESCRIPTION OF THE DRAWINGS

FIG. 3 depicts stability profiles of different tablet formulations of quinapril sodium.

FIG. 4 depicts impurity levels in different formulations of quinapril sodium.

Figure 1:
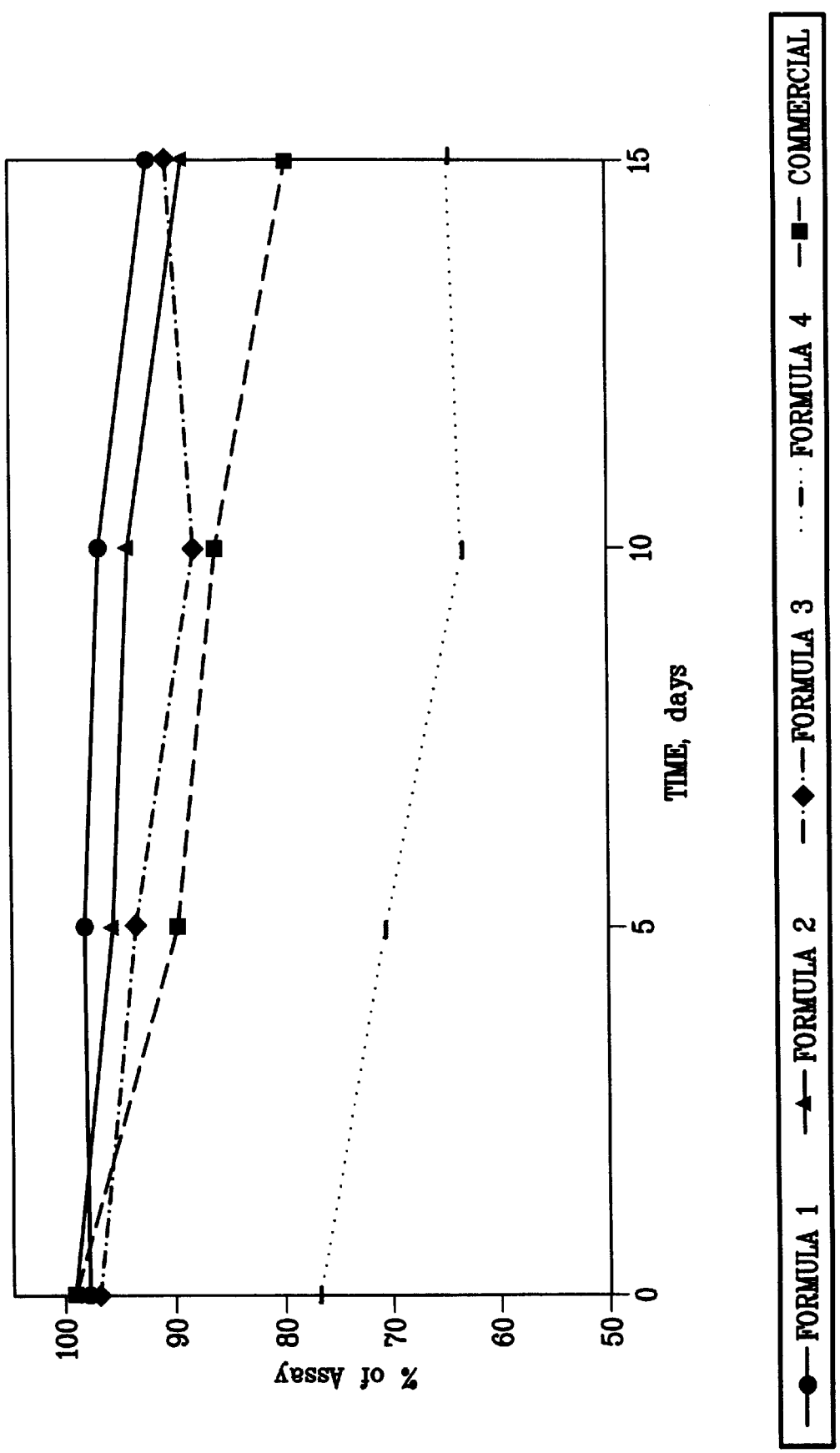
FIG. 1 depicts stability profiles of different formulations of enalapril sodium.

The practice of the present invention employs, unless otherwise indicated, conventional methods of chemistry and drug synthesis and formulation, all within the skill of the art. Such techniques are explained fully in the literature. See, e.g., Remington's Pharmaceutical Sciences, 18th Edition (Easton, Pa.: Mack Publishing Company, 1990), incorporated herein by reference.

The present invention arises from the surprising discovery that it is possible to provide for the rapid, economical preparation of ACE inhibitors while minimizing breakdown of the product and maximizing the final purity of that product. Breakdown may be due to factors including, but not limited to, hydrolysis and cyclization. Cyclization may be due to factors including, but not limited to, internal nucleophilic attack. Formulations of stabilized ACE inhibitors, especially those of enalapril sodium and quinapril hydrochloride, are also provided. Although not wishing to be bound by theory, the inventor believes that the presence of alcohol, as described hereinafter, not only accelerates the manufacture of the product but also minimizes extensive hydrolysis and/or cyclization of the product during production and storage. Surprisingly, it has also been found that the presence of cellulosic materials in the present method results in formulations that are substantially free of breakdown products; in the case of enalapril maleate, resulting in formulations which are substantially free of enalaprilat and/or enalapril-DKP, or, in the case of quinapril hydrochloride, substantially free of quinaprilat and/or quinapril-DKP.

As used herein, the phrase "stabilized ACE inhibitor" refers to ACE inhibitors prepared according to the present invention, and is meant to encompass an ACE inhibitor salt with a metal compound. As used herein, the term "DKP" or "diketopiperazine" includes DKP-compounds of the ACE inhibitor. For example, the DKP breakdown product of enalapril maleate, enalapril-DKP, is encompassed by the term "DKP" or "diketopiperazine".

The term "substantially free" refers to compositions that have significantly reduced levels of detectable breakdown products, e.g. enalaprilat and/or enalapril-DKP in the case of enalapril maleate, or quinaprilat and/or quinapril-DKP in the case of quinapril hydrochloride. In one embodiment, the enalapril sodium contains less than about 5% enalaprilat, preferably less than 2.5% enalaprilat, or, even more preferably, less than about 1%, or, in the case of other ACE inhibitors, a similarly small quantity of analogous impurity. In another embodiment, the enalapril sodium contains less than about 1.0% DKP, more preferably less than about 0.5% DKP, or, even more preferably, less than about 0.25% DKP or, in the case of other ACE inhibitors, a similarly small quantity of analogous impurity. In another embodiment, the quinapril sodium contains less than about 7.5% quinaprilat, preferably less than about 5% quinaprilat, more preferably less than about 2.5% quinaprilat, or, even more preferably, less than about 1% quinaprilat. In another embodiment, the quinapril sodium contains less than about 5.0% DKP, preferably less than about 1% DKP, more preferably less than about 0.5% DKP, or, even more preferably, less than about 0.25% DKP. In another embodiment, the quinapril sodium contains less than about 5% quinaprilat and less than about 1% DKP.

As used herein, the terms "analogous breakdown product", "degradation product", or "analogous impurity" or derivatives thereof, refer to undesired contaminants formed by breakdown of an ACE inhibitor which are similar, as appreciated by persons of ordinary skill in the art, to those resulting from ACE inhibitor breakdown. Breakdown of ACE inhibitors may be caused by factors including, but not limited to, hydrolysis and cyclization.

The present invention provides methods of preparing stable formulations of ACE inhibitors, especially enalapril maleate and quinapril hydrochloride. The methods comprise the steps of mixing an ACE inhibitor, for example enalapril maleate, with an alcohol to form an alcoholic dispersion, dissolving or dispersing a metal compound in water to form a metal compound solution or dispersion, and mixing together the alcoholic dispersion of the ACE inhibitor and the aqueous solution or dispersion of the metal compound. In some embodiments, the mixture of the alcoholic dispersion is mixed with the aqueous solution or dispersion of the metal compound until a clear solution is attained. In other embodiments the method further comprises adding at least one excipient to the clear solution. Alternative embodiments further comprise adding an antioxidant to the alcoholic dispersion. Some embodiments further comprise blending at least one excipient and the clear solution to form a granulate. In other embodiments, the granulates are dried and preferably processed into a pharmaceutical solid, e.g. tablet, particulate and the like.

As used herein, the term "alcohol" refers to lower, e.g. $C_1$ to $C_6$, monohydric alcohols acceptable for pharmaceutical preparations, especially ethanol. While polyhydric alcohols may be used, they are generally more toxic and are not preferred. The terms "alcohol" and "alcoholic" include water/alcohol mixtures—hydroalcoholic systems.

As used herein, the term "metal compound" refers to a compound added to the ACE inhibitor to effect its conversion to the stabilized ACE inhibitor. Metal compounds useful in connection with this invention are basic salts of alkali and alkaline earth metals which are readily water soluble and which do not interfere with the stability of the compositions of the present invention. Thus, the readily water and/or alcohol-soluble salts of lithium, sodium, potassium, cesium, rubidium, calcium, magnesium, strontium and barium, bicarbonate, carbonate, hydroxide, acetate, borate and similar materials may be employed herein as the metal compound. Preferred among these are sodium, potassium, calcium, and magnesium salts, especially sodium salts. Counterions which are preferred are bicarbonate, hydroxide and carbonate, with bicarbonate being most preferred. Sodium bicarbonate is most preferred for certain embodiments of the invention. This includes, but is not limited to, sodium bicarbonate, sodium hydroxide, sodium acetate, and sodium borate. While sodium is the conventional and preferred ion, potassium and other pharmaceutically acceptable anions may be employed and all such will be understood to be encompassed hereby.

As used herein, the term "antioxidant" refers to a composition which reduces or prevents oxidation. "Antioxidants" include, but are not limited to, butyl hydroxyl anisol (BHA), butyl hydroxyl toluene (BHT), maleic acid, and ascorbic acid. In a preferred embodiment the antioxidant is maleic acid, and is present in an amount from about 0.001% to about 2.0% w/w per unit dose.

In one embodiment of the present invention, the method further comprises the addition of a thickening agent to the metal compound solution or dispersion. As used herein, the term "thickening agent" is well known to those of skill in the art. A wide variety of thickening agents may be used to prepare the stable formulations of the present invention. Suitable thickening agents include any and all biocompatible agents known to function as thickening agents. In a preferred embodiment of the present invention, the thickening agent is selected from the group consisting of polyethylene glycol, propylene glycol, glycerin, cross-linked povidone, polyvinylpyrrolidone, and modified celluloses known to form hydrocolloids, such as hydroxypropylmethylcellulose. In a more preferred embodiment, the thickening agent is polyvinylpyrrolidone, and is present in an amount from about 1% to about 5% w/w per unit dose.

Tabletting and other pharmaceutically acceptable excipients may be blended with the dry material provided hereby to facilitate formation of conventional and convenient pharmaceutical solids. Such formulation is known per se.

As used herein, the term "clear solution" refers to the solution attained after complete or substantially complete conversion of the ACE inhibitor to the stabilized ACE inhibitor. The term "clear solution" may refer to a substantially clear material having some coloration, typically a yellowish tint, which may appear to be colloidal. This definition includes solutions which are partly cloudy. For example, as used for the end-point for complete conversion of enalapril maleate to enalapril sodium or for the complete conversion of quinapril hydrochloride to quinapril sodium, the term "clear solution" refers to the relative absence of foamation or bubbling. The presence of a "clear solution" is measured by eye, assessing the absence of foamation.

The term "excipient" includes, but is not limited to, the family of modified celluloses such as carboxymethyl and ethyl cellulose, hydroxyethyl cellulose, hydroxypropyl cellulose, microcrystalline cellulose, cross-linked povidone, hydroxypropylmethylcellulose and others. In one embodiment, the excipient is at least one of microcrystalline cellulose, starch, and sodium starch glycolate.

In one embodiment of the present invention, a pharmaceutical preparation comprising a pharmaceutically acceptable salt of a stabilized ACE inhibitor substantially free of breakdown products is provided. In a preferred embodiment, the ACE inhibitor is enalapril maleate, the stabilized ACE inhibitor is enalapril sodium, and the breakdown products are enalaprilat and/or enalapril-DKP. In another preferred embodiment, the ACE inhibitor is quinapril hydrochloride, the stabilized ACE inhibitor is quinapril sodium, and the breakdown products are quinaprilat and/or quinapril-DKP.

In still another embodiment of the present invention, pharmaceutical preparations are provided comprising a pharmaceutically acceptable salt of a stabilized ACE inhibitor and microcrystalline cellulose, substantially free of breakdown products. In a preferred embodiment, the ACE inhibitor is enalapril maleate or quinapril hydrochloride, the stabilized ACE inhibitor is enalapril sodium or quinapril sodium, and the breakdown products are enalaprilat and/or enalapril-DKP, or quinaprilat and/or quinapril-DKP.

Microcrystalline cellulose is known per se and a variety of such are commercially available. Exemplary among these is the family of products sold by the FMC Corporation under the trademark Avicel®. Any of the members of this family may be used in connection with the practice of one or more embodiments of the present invention and all are contemplated hereby. Other cellulose products which are similar in nature to microcrystalline cellulose may find utility herein, such a parenchymal cell cellulose.

In addition to the preferred microcrystalline celluloses and similar materials, other cellulosic materials may also be employed in connection with one or more embodiments of the present invention. Thus, modified celluloses such as methyl cellulose, hydroxyethyl cellulose, hydroxypropyl cellulose, methylhydroxyethyl cellulose, methylhydroxypropyl cellulose, carboxymethyl cellulose salts and esters, (e.g. sodium, potassium etc. salts), and other cellulose derivatives may be so employed. It will be appreciated by persons of ordinary skill in the art that such cellulosic materials should be consistent with the overall spirit of the invention. Thus, such materials may be employed which do not adversely effect the processing set forth herein and which do not interfere with the stability of the resulting products.

Those of skill in the art will also understand that the term "excipient" is used colloquially to include such agents as disintegrating agents, carriers, diluents, pigments, binders, colorants, and lubricants. In one embodiment, the excipient is a disintegrating agent.

The term "disintegrating agent" is well known to those of skill in the art as an agent that enhances the conversion of a compact material into fine primary particles during dissolution. Disintegrating agents include, but are not limited to, starch, cellulose, sodium starch glycolate, cross-linked povidones, and modified celluloses, and are present in amounts from about 1% to about 25% w/w per unit dose.

The term "lubricant" is well known to those of skill in the art as an additive to prevent the sticking of the formulation to tooling during the tabletting process. Lubricants include, but are not limited to, stearates, hydrogenated vegetable oils, and talc. In some embodiments of the present invention, the lubricant is a stearate. In some preferred embodiments, the lubricant is magnesium stearate or glyceryl monostearate and is present in an amount from about 0.5% to about 10% w/w per unit dose. In a more preferred embodiment, the lubricant is magnesium stearate and is present in an amount from about 0.01% to about 1% w/w per unit dose.

The term "binder" is well known to those of skill in the art as an agent that holds the components of the formulation together. Binders include, but are not limited to, gelatin, polyvinylpyrrolidone (PVP), hydroxypropylmethylcellulose (HPMC), starch grades (pregelatinized or plain), hydroxypropylcellulose (HPC), and carboxymethylcellulose (CMC), and their salts.

As used herein, the term "drying" refers to the substantial removal of liquid from the granulation. Drying may be accomplished in a number of manners well known to those of skill in the art including, but not limited to the use of ovens, fluid bed driers, and other similar equipment. In a preferred embodiment, the granulation is dried for about 12 hours at 50° C. to substantially remove liquid from the granulation.

As used herein, the term "pharmaceutical solid dosage forms" refers to the final solid pharmaceutical product. The term "pharmaceutical solid dosage form" includes, but is not limited to, tablets, caplets, beads, and capsules (including both hard shell capsules and soft gelatin capsules).

The processes of mixing, drying, granulating and making pharmaceutical solid formulations are well known to those of skill in the art. See, e.g., Theory & Practice of Industrial Pharmacy, $3^{rd}$ Edition, Liberman, Lachman, and Kanig, eds. (Philadelphia, Pa.: Lea & Febiger), incorporated herein by reference.

By "pharmaceutically acceptable" or "pharmacologically acceptable" is meant a material which is not biologically or otherwise undesirable, i.e., the material can be administered to an individual along with the stabilized ACE inhibitor formulation without causing any undesirable biological effects or interacting in a deleterious manner with any of the components of the formulation in which it is contained.

EXAMPLES

Below are several examples of specific embodiments for carrying out the present invention. The examples are offered for illustrative purposes only, and are not intended to limit the scope of the present invention in any way.

Example 1

Materials and Methods

In the following formulations, the quantities of ingredients are provided in equivalent weights (in mg per unit dose (mg/ud)). The approximate batch dose was about 6000 units.

Preparation of Formula I

Enalapril maleate (20 mg/ud; Byron Chem. Co., Long Island City, N.Y.) was suspended in denatured alcohol (50 mg/ud, SD3A) with stirring at 500 rpm. Full dispersion of the enalapril maleate in the alcohol was achieved in less than about 10 seconds. In a separate container, sodium bicarbonate (11 mg/ud) and povidone (polyvinylpyrrolidone; Plasdone®, ISP, Bound Brook, N.J.) were dissolved in 100 mg/ud purified water (USP). The sodium bicarbonate/povidone solution was added gradually to the alcoholic drug dispersion with constant stirring (200 rpm) until a clear solution was achieved to yield solution 1, e.g. the solution was free of foaming (bubbling).

Microcrystalline cellulose (225 mg/ud, Avicel® PH200; FMC Corporation, Philadelphia, Pa.), sodium starch glycolate (30 mg/ud, Explotab®; Edward Mendell Co., New York, N.Y.), and silicon dioxide (8 mg/ud; Syloid® 244 FP; W.R. Grace & Co., Baltimore, Md.) were mixed for three minutes in a high shear mixer for 3 minutes (Collete Gral 10, Machines Collette, Belgium) to yield mixture 1. Mixture 1 was blended with solution 1 for three minutes at low speed with the choppers set to low. The resulting granulation was then dried for 12 hours at 50° C. The dried granulation was then passed through a #30 mesh screen and blended with magnesium stearate (2 mg/ud), producing the final tabletting blend of Formula I.

Preparation of Formula II

Formula II was synthesized according to the methods set forth for Formula I with the following variation. Enalapril maleate was suspended in denatured alcohol (30 mg/ud, SD3A) and Tween8® (polysorbate 80; 20 mg/ud; Sigma, St. Louis, Mo.) with stirring at 500 rpm.

Preparation of Formula III

Enalapril maleate (20 mg/ud; Byron Chem. Co., Long Island City, N.Y.) was suspended in purified water (50 mg/ud, USP) with stirring at 500 rpm. In a separate container, sodium bicarbonate (11 mg/ud) and povidone (9 mg/ud; PVP K29/32) were dissolved in purified water (100 mg/ud, USP). The sodium bicarbonate/povidone solution was added gradually to the drug dispersion with constant stirring (200 rpm) until an almost clear solution was achieved to yield solution 2.

Microcrystalline cellulose (225 mg/ud; Avicel® PH200; FMC, Philadelphia, Pa.), sodium starch glycolate (30 mg/ud, Explotab®; Edward Mendell Co., New York, N.Y.), and silicon dioxide (8 mg/ud, Syloid® 244 FP; W.R. Grace & Co., Baltimore, Md.) were mixed for three minutes in a high shear mixer for 3 minutes (Collete Gral 10) to yield mixture 2. Mixture 2 was blended with solution 2 for three minutes at low speed with the choppers set to low. The resulting granulation was then dried for 12 hours at 50° C. The dried granulation was then passed through a #30 mesh screen and blended with magnesium stearate (2 mg/ud), producing the final tabletting blend of Formula III.

Preparation of Formula IV

Formula IV was synthesized according to the methods set forth for Formula III with the following variation. Enalapril maleate was suspended in purified water (30 mg/ud, SD3A) and Tween® 80 (20 mg/ud; Sigma, St. Louis, Mo.) with stirring at 500 rpm.

Formulations I and II were made according to the present invention, while Formulations III and IV were made according to Merslavic et al. in terms of conversion of enalapril maleate to enalapril sodium. However, unlike the methods described in Merslavic et al., Formulations III and IV were prepared using microcrystalline cellulose instead of starch and cellulose as the diluent. Formulation IV further contained Tween 80® dispersed in water to increase the wetting properties of enalapril maleate.

Preparation of Formula V

Purified water (50 mg/ud, USP) was mixed with alcohol (40 mg/ud, SD3A) in a glass beaker using a Lightnin Mixer at 500 rpm. Quinapril HCl (20 grams, Gyma Laboratories, Westbury, N.Y.) was mixed into the water/alcohol mixture using a Lightnin Mixer at 500 rpm to yield suspension 1. Sodium bicarbonate (11 mg/ud) was slowly added to suspension 1 with stirring using a Lightnin Mixer at 500 rpm until a clear to almost clear solution was attained, with no bubbling or foaming. Povidone (9 mg/ud, PVP K29/32) was then added to the clear/almost clear solution and mixed using a Lightnin Mixer until a uniform solution was attained. Syloid® (30 mg/ud, 244 FP) was then added and mixed until a uniform solution was attained to form solution 1.

Microcrystalline cellulose (70 mg/ud, Avicel® PH101; FMC Corporation, Philadelphia, Pa.) was mixed with sodium starch glycolate (15 mg/ud, Explotab®; Edward Mendell Co., New York, N.Y.) were mixed for five minutes in a high shear mixer (Collete Gral 10) to form mixture 1. The entirety of solution 1 was then added at once to mixture 1 and granulated for 5 minutes in a high shear mixer (Collete Gral 10), with the paddles and choppers set to low speed.

The resulting granulation was then dried for 10 hours at 45° C.–50° C. The dried granulation was then passed through a 0.065 RD stainless steel screen using a Fitzmill Comminutor (Model L1A; Fitzpatrick Co., Elmhurst, Ill.) set at high speed, producing blend 1, also named Formula V powder form.

Microcrystalline cellulose (95 mg/ud) and sodium starch glycolate (3 mg/ud) were added to blend 1 in a 16 quart Gemco blender (double cone mixer; Gemco) and mixed for 5 minutes to yield blend 2. Magnesium stearate (2 mg/ud; NF; Mallinckrodt Inc., St Louis, Mo.) was passed through a #30 mesh stainless steel screen and then added to blend 2 and mixed for 1 minute to yield blend 3. Blend 3 was compressed into tablets of about 250 mg weight, also named Formula V tablet form. The tablets had an approximate hardness of 15–20 kp, measured using a Schleuinger Model D6 hardness tester (Dr. Schleuinger Pharmatrone, Manchester, N.H.).

Preparation of Formula VI

Purified water (75 mg/ud, USP) was mixed with alcohol (40 mg/ud, SD3A) in a glass beaker using a Lightnin Mixer at 500 rpm. Quinapril HCl (20 mg/ud) were mixed into the water/alcohol mixture using a Lightnin Mixer at 500 rpm to yield suspension 1. Sodium bicarbonate (11 mg/ud) was slowly added to suspension 1 with stirring using a Lightnin Mixer at 500 rpm until a clear to almost clear solution was attained, with no bubbling or foaming. Povidone (9 mg/ud, PVP K29/32) was then added to the clear/almost clear solution and mixed using a Lightnin Mixer until a uniform solution was attained, solution 1.

Microcrystalline cellulose (100 mg/ud, Avicel® PH101; FMC Corporation, Philadelphia, Pa.) was mixed with sodium starch glycolate (3 mg/ud, Explotab®; Edward Mendell Co., New York, N.Y.) were mixed for five minutes in a high shear mixer (Collete Gral 10) to form mixture 1. The entirety of solution 1 was then added at once to mixture 1 and granulated for 5 minutes in a high shear mixer (Collete Gral 10), with the paddles and choppers set to low speed.

The resulting granulation was then dried for 10 hours at 45° C.–50° C. The dried granulation was then passed through a 0.065 RD stainless steel screen using a Fitzmill Comminutor (Model L1A) set at high speed, producing blend 1, also named Formula VI powder form.

Microcrystalline cellulose (95 mg/ud) and sodium starch glycolate (3 mg/ud) were added to blend 1 in a 16 quart Gemco blender (double cone mixer; Gemco) and mixed for 5 minutes to yield blend 2. Magnesium stearate (2 mg/ud; NF) was passed through a #30 mesh stainless steel screen and then added to blend 2 and mixed for 1 minute to yield blend 3. Blend 3 was compressed into tablets of about 250 mg weight with an approximate hardness of 15–20 kp, also named Formula VI tablet form.

Preparation of Formula VII

Purified water (15.5 mg/ud, USP) was mixed with alcohol (40 mg/ud, SD3A) in a glass beaker using a Lightnin Mixer at 500 rpm. Quinapril HCl (20 mg/ud) were mixed into the water/alcohol mixture using a Lightnin Mixer at 500 rpm to yield suspension 1. Sodium bicarbonate (11 mg/ud) was slowly added to suspension 1 with stirring using a Lightnin Mixer at 500 rpm until a clear to almost clear solution was attained, with no bubbling or foaming. Povidone (9 mg/ud, PVP K29/32) was then added to the clear/almost clear solution and mixed using a Lightnin Mixer until a uniform solution was attained, solution 1.

Microcrystalline cellulose (95 mg/ud, Avicel® PH101; FMC Corporation, Philadelphia, Pa.) was mixed with sodium starch glycolate (15 mg/ud, Explotab®; Edward Mendell Co., New York, N.Y.) were mixed for five minutes in a high shear mixer (Collete Gral 10) to form mixture 1. The entirety of solution 1 was then added at once to mixture 1 and granulated for 5 minutes in a high shear mixer (Collete Gral 10), with the paddles and choppers set to low speed.

The resulting granulation was then dried for 10 hours at 45° C.–50° C. The dried granulation was then passed through a 0.065 RD stainless steel screen using a Fitzmill Comminutor (Model L1A) set at high speed, producing blend 1, also named Formula VII powder form.

Microcrystalline cellulose (95 mg/ud) and sodium starch glycolate (3 mg/ud) were added to blend 1 in a 16 quart Gemco blender and mixed for 5 minutes to yield blend 2. Magnesium stearate (2 mg/ud; NF) was passed through a #30 mesh stainless steel screen and then added to blend 2 and mixed for 1 minute to yield blend 3. Blend 3 was compressed into tablets of about 250 mg weight with an approximate hardness of 15–20 kp, also named Formula VII tablet form.

Example 2

Comparison of Stability Profiles of Different Formulations of Enalapril Sodium

The stability profiles of different formulations of enalapril sodium were compared. The stability of formulations of enalapril sodium (Formulas I–IV, as described above) were also compared to a commercial formulation of enalapril maleate, VASOTEC™ (Merck & Co.) referred to as "Enalapril-commercial." Formulations were stored at 60° C. with 75% relative humidity to simulate extended storage. Stability of the formulations was assessed at 5, 10, and 15 days by HPLC.

As shown in FIG. 1, Formulation I was more stable than the VASOTEC™ formulation and Formulations II–IV at the 5, 10, and 15 day timepoints. At the 5 and 10 day timepoints, Formulation II exhibited greater stability than Formulations III, IV, and the VASOTEC™ formulation, referred to as the "Enalapril-commercial." Formulation II was more stable at the 5, 10, and 15 day timepoints than the VASOTEC™ formulation and Formulation IV.

Example 3

Comparison of Levels of Impurities in Different Formulations of Enalapril Sodium The levels of impurities in different formulations of enalapril sodium were compared. The level of impurities of the formulations of enalapril sodium were also compared to a commercial formulation of enalapril maleate, VASOTEC™. Formulations were stored at 60° C. with 75% relative humidity to simulate extended storage. Impurity levels of the formulations were assessed at 5, 10, and 15 days by measurement of enalaprilat and enalapril-DKP formation by HPLC.

Figure 2:
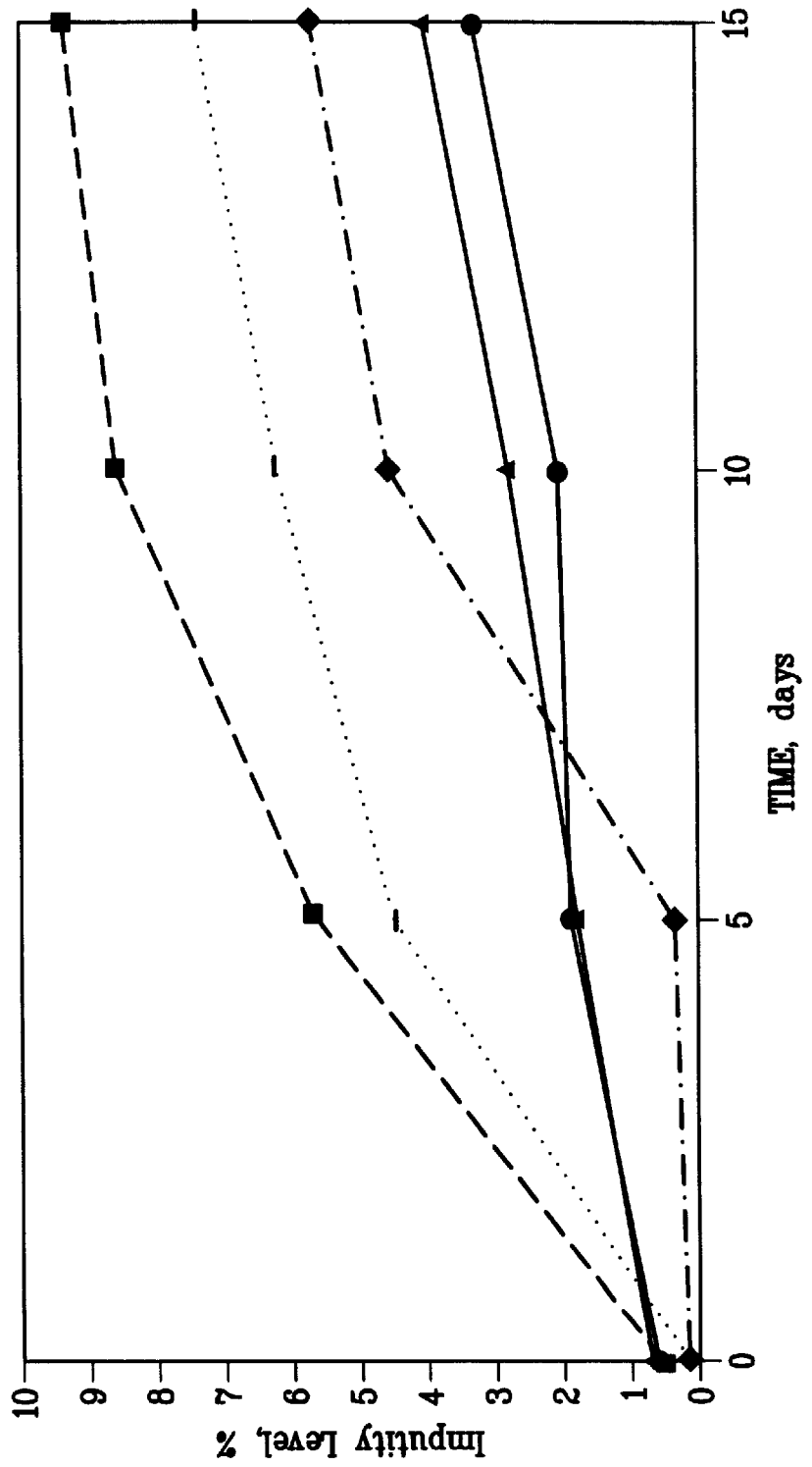
FIG. 2 depicts impurity levels in different formulations of enalapril sodium.

As shown in FIG. 2, at the 10 and 15 day timepoints, Formulation I exhibited the greatest purity; e.g. the lowest level of impurity. At the 10 and 15 day timepoints, Formulation I had less impurities than did Formulations II, IV, and VASOTEC™.

Formulation II exhibited less impurities than did Formulations III, IV, and VASOTEC™ at the 10 and 15 day timepoints.

Example 4

Effect of Alcohol/Water Ratio on Dispersion Time of Enalapril Maleate

Enalapril maleate (50 grams) were added to 200 mL of liquid. The liquid ranged from 100% alcohol/0% water to 0% alcohol/100% water (USP) (see Table 1). The solutions were stirred at 200 rpm at room temperature using a Lightnin® Mixer (General Signal Controls, Rochester, N.Y.) with the mixing blade 1 cm from the bottom of the beaker. Enalapril maleate was considered "dispersed" when all of the drug powder was wetted and had become immersed in the liquid.

As shown in Table 1, solutions containing high relative levels of alcohol yielded faster dispersion of enalapril maleate than did solutions containing lower relative levels of alcohol. Surprisingly, an enalapril maleate suspension containing 100% alcohol had a dispersion time of 27 seconds whereas an enalapril maleate suspension containing 100% water had a dispersion time of over 76 minutes.

TABLE 1

Dispersion time of enalapril maleate increased as the proportion of water in the liquid solution increased.

| % Alcohol/% Water | Volume Alcohol/Volume Water | Dispersion Time |
|---|---|---|
| 100%/0% | 200 mL/0 mL | 27 seconds |
| 85%/15% | 170 mL/30 mL | 28 seconds |

TABLE 1-continued

Dispersion time of enalapril maleate increased as the proportion of water in the liquid solution increased.

| % Alcohol/% Water | Volume Alcohol/Volume Water | Dispersion Time |
|---|---|---|
| 75%/25% | 150 mL/50 mL | 30 seconds |
| 50%/50% | 100 mL/100 mL | 45 seconds |
| 25%/75% | 50 mL/150 mL | 1 minute, 15 seconds |
| 0%/100% | 0 mL/200 mL | 76 minutes, 43 seconds |

Example 5

Comparison of Stability Profiles of Different Formulations of Quinapril Sodium

The level of impurities of the formulations of quinapril sodium were compared to a commercial formulation of ACCUPRIL™ (Parke-Davis), referred to as "Quinapril-commercial." Formulations were stored at 60° C. with 75% relative humidity to simulate extended storage. Impurity levels of the formulations were assessed at 5, 10, and 15 days by measurement of quinaprilat and quinapril-DKP formation by HPLC. Formulations were stored at 60° C. with 75% relative humidity to simulate extended storage. The ACCUPRIL™ formulation was placed in a 60 cc HDPE bottle with a 33 mm metal cap with no dessicant and no dunnage. Formulations V–VII in tablet from were placed in a 60 cc HDPE bottle with a 33 mm metal cap with no dessicant and no dunnage. Stability of the formulations was assessed at 5, 10, and 15 days by HPLC.

As shown in FIG. 3, at the 5, 10, and 15 day timepoints, Formulations V–VII in tablet form exhibited greater purity in terms of quinaprilat content than did the ACCUPRIL™ tablet.

Example 6

Comparison of Levels of Impurities in Different Formulations of Quinapril Sodium The levels of impurities in different formulations of quinapril sodium were compared. The level of impurities of the formulations of quinapril sodium were also compared to a commercial formulation of quinapril HCl, ACCUPRIL™ (Parke-Davis). Formulations were stored at 60° C. with 75% relative humidity to simulate extended storage. Impurity levels of the formulations were assessed at 5, 10, and 15 days by measurement of quinaprilat and quinapril-DKP formation by HPLC.

As shown in FIG. 4, at all timepoints Formulations V–VII exhibited greater purity; e.g. the lowest level of impurity, than did the commercial formulation.

The present invention has been exemplified with respect to the pharmaceuticals enalapril maleate and quinapril hydrochloride. Persons of ordinary skill in the art will appreciate, however, that certain other drugs known to be ACE inhibitors may also suffer from the same shortcomings as enalapril maleate and/or quinapril hydrochloride. The members of this class of ACE inhibitors may also benefit from employment of the present invention, and all such drugs are contemplated hereby. Among this class are the drugs lisinopril, benazepril, ramipril, indolapril and moexipril, known per se.

All publications, patents and patent applications cited herein are hereby incorporated by reference in their entirety. As used in this specification and the appended claims, the singular forms "a," "an" and "the" include plural references unless the content clearly dictates otherwise. Thus, for example, reference to "an excipient" includes a mixture of two or more excipients.

What is claimed is:

1. A method of preparing a stable formulation of ACE inhibitor which comprises the steps of:

mixing an ACE inhibitor with an alcohol to form an alcoholic dispersion;

dispersing or dissolving a metal compound in water to form a metal compound dispersion or solution;

mixing the alcoholic dispersion and the metal compound dispersion until a clear solution is attained;

adding at least one excipient to the clear solution;

blending the excipient and the clear solution to form a granulate;

drying the granulate; and adding a lubricant to the dried granulate wherein the lubricant is selected from the group consisting of stearates, hydrogenated vegetable oils, and talc.

2. The method of claim 1 wherein said lubricant is a stearate.

3. The method of claim 2 wherein said stearate is selected from the group consisting of magnesium stearate and glyceryl monostearate.

* * * * *